(12) United States Patent
Bo et al.

(10) Patent No.: US 11,393,558 B2
(45) Date of Patent: Jul. 19, 2022

(54) METHODS, CIRCUITS, SYSTEMS, AND ARTICLES OF MANUFACTURE FOR SEARCHING A REFERENCE SEQUENCE FOR A TARGET SEQUENCE WITHIN A SPECIFIED DISTANCE

(71) Applicant: University of Virginia Patent Foundation, Charlottesville, VA (US)

(72) Inventors: Chunkun Bo, Charlottesville, VA (US); Kevin Skadron, Charlottesville, VA (US); Elaheh Sadredini, Charlottesville, VA (US); Vinh Dang, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1170 days.

(21) Appl. No.: 15/932,287

(22) Filed: Feb. 16, 2018

(65) Prior Publication Data

US 2019/0258777 A1  Aug. 22, 2019

(51) Int. Cl.
*G16B 30/00* (2019.01)
*G06N 5/04* (2006.01)
*G06F 16/903* (2019.01)

(52) U.S. Cl.
CPC ....... *G16B 30/00* (2019.02); *G06F 16/90344* (2019.01); *G06N 5/047* (2013.01)

(58) Field of Classification Search
None
See application file for complete search history.

(56) References Cited

PUBLICATIONS

Thomas et al. Decombinator: a tool for fast, efficient gene assignment in T-cell receptor sequences using a finite state machine Bioinformatics vol. 29, pp. 542-550 (Year: 2013).*
Rasool et al. String Matching Methodologies: A Comparative Analysis International Journal of Computer Science and Information Technologies vol. 3, pp. 3394-3397 (Year: 2012).*
Wagner Clock System Design IEEE Design & Test of Computers vol. 5, pp. 9-27 (Year: 1988).*
Xie, et al.; *REAPR: Reconfigurable Engine for Automata Processing*; Department of Electrical and Computer Engineering, University of Virginia Department of Computer Science, University of Virginia.
Dlugosch, et al.; *An Efficient and Scalable Semiconductor Architecture for Parallel Automata Processing*; IEEE Transactions on Parallel and Distributed Systems, vol. 25, No. 12; Dec. 2014; pp. 3088-3098.
Cascarano, et al.; *Public Review for iNFAnt: NFA Pattern Matching on GPGPU Devices*, ACM SIGCOMM Computer Communication Review; vol. 40, No. 5, Oct. 2010; pp. 20-26.
Roy, et al.; *Finding Motifs in Biological Sequences using the Micron Automata Processor*; 2014 IEEE 28$^{th}$ International Parallel & Distributed Processing Symposium; (2014), pp. 416-424.
Bae, et al. *Cas-OFFinder: a Fast and Versatile Algorithm that Searches for Potential Off-Target Sites of Cas9 RNA-guided Endonucleases*, BIOINFORMATICS Applications Note; vol. 30 No. 10; (2014), pp. 1473-1475.
Xiao, et al.; *CasOT: A Genome-Wide Cas9/gRNA Off-Target Searching Tool*, BIOINFORMATICS Applications Note, vol. 30, No. 8, pp. 1180-1182.
Bo et al., "Searching for Potential gRNA Off-Target Sites for CRISPR/Cas9 using Automata Processing across Different Platforms," HPCA 2018.
Jay Bennett, "11 Crazy Gene-Hacking Things We Can Do with CRISPR," http://www.popularmechancis.com/science/a19067/11-crazy-things-we-can-do-with-crispr-cas9/, Popular Mechanics, Jan. 26, 2016, 4 pages.
"SDAccel Development Environment," https://www.xilinx.com/products/design-tools/software-zone/sdaccel.html, Printed from the Internet Jun. 11, 2019.
Cheng et al. "Approximate string matching in DNA sequences" *Eighth International Conference on Database Systems for Advanced Applications*, 2003. (DASFAA 2003). Proceedings. DOI: 10.1109/DASFAA.2003.1192395.

* cited by examiner

*Primary Examiner* — John S Brusca
(74) *Attorney, Agent, or Firm* — Stanek Lemon Crouse & Meeks, P.A.

(57) ABSTRACT

A method of operating a finite state machine circuit can be provided by determining if a target sequence of characters included in a string of reference characters occurs within a specified difference distance using states indicated by the finite state machine circuit to indicate a number of character mis-matches between the target sequence of characters and a respective sequence of characters within the string of reference characters.

18 Claims, 12 Drawing Sheets

Specification includes a Sequence Listing.

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial
<220> FEATURE:
<223> OTHER INFORMATION: gRNA target sequence

<400> SEQUENCE: 1
taatatagat tagccattat                                              20

<210> SEQ ID NO 2
<211> LENGTH: 12
<212> TYPE: DNA
<213> ORGANISM: Artificial
<220> FEATURE:
<223> OTHER INFORMATION: gRNA target sequence

<400> SEQUENCE: 2
tctagagcag ta                                                      12

<210> SEQ ID NO 3
<211> LENGTH: 12
<212> TYPE: DNA
<213> ORGANISM: Artificial
<220> FEATURE:
<223> OTHER INFORMATION: gDNA target sequence

<400> SEQUENCE: 3
tactgctcta ga                                                      12

<210> SEQ ID NO 4
<211> LENGTH: 19
<212> TYPE: DNA
<213> ORGANISM: Artificial
<220> FEATURE:
<223> OTHER INFORMATION: Reference genome sequence
```

```
<400> SEQUENCE: 4
taatatagat tagccatta                                               19

<210> SEQ ID NO 5
<211> LENGTH: 19
<212> TYPE: DNA
<213> ORGANISM: Artificial
<220> FEATURE:
<223> OTHER INFORMATION: Reference genome sequence

<400> SEQUENCE: 5
aatatagatt agccattat                                               19

<210> SEQ ID NO 6
<211> LENGTH: 11
<212> TYPE: DNA
<213> ORGANISM: Artificial
<220> FEATURE:
<223> OTHER INFORMATION: Reference genome sequence

<400> SEQUENCE: 6
tctagagcag t                                                       11

<210> SEQ ID NO 7
<211> LENGTH: 11
<212> TYPE: DNA
<213> ORGANISM: Artificial
<220> FEATURE:
<223> OTHER INFORMATION: Reference genome sequence

<400> SEQUENCE: 7
ctagagcagt a                                                       11

<210> SEQ ID NO 8
<211> LENGTH: 11
<212> TYPE: DNA
<213> ORGANISM: Artificial
<220> FEATURE:
<223> OTHER INFORMATION: Reference gemone sequence

<400> SEQUENCE: 8
tactgctcta g                                                       11

<210> SEQ ID NO 9
<211> LENGTH: 11
<212> TYPE: DNA
<213> ORGANISM: Artificial
<220> FEATURE:
<223> OTHER INFORMATION: Reference genome sequence

<400> SEQUENCE: 9
actgctctag a                                                       11
```

METHODS, CIRCUITS, SYSTEMS, AND ARTICLES OF MANUFACTURE FOR SEARCHING A REFERENCE SEQUENCE FOR A TARGET SEQUENCE WITHIN A SPECIFIED DISTANCE

STATEMENT OF FEDERAL SUPPORT

This invention was made with government support under Grant No. HR0011-13-3-0002 awarded by the Department of Defense/Defense Advanced Research Projects Agency (DARPA). The government has certain rights in the invention.

STATEMENT REGARDING ELECTRONIC FILING OF A SEQUENCE LISTING

A Sequence Listing in ASCII text format, submitted under 37 C.F.R. § 1.821, entitled 170964-00004v2_ST25.txt, 2,090 bytes in size, generated on Jul. 19, 2021, and filed via EFS-Web, is provided in lieu of a paper copy. This Sequence Listing is hereby incorporated herein by reference into the specification for its disclosures.

BACKGROUND

Clustered Regularly Interspaced Short Palindromic Repeats (CRISPR) exist in prokaryotic DNAs. The CRISPR/Cas9 system is an immune system which can defend against foreign genetic elements. CRISPR/Cas9 is one version of the system that attracts researchers' interest, because it can be modified to edit genomes. One can deliver the Cas9 nuclease together with a guide RNA (gRNA) into a cell and edit the cell's genome at targeted locations (or sequences) that are defined by the gRNA.

Genome editing using CRISPR/Cas9 has been a popular technique since it was first introduced. For example, researchers may use cells edited by CRISPR/Cas9 to target cancers. The CRISPR/Cas9 system is also being used to treat other diseases with genetic causes, such as amnesia, muscular dystrophy, etc. However, efficiently finding all correct locations to edit the genome, without modifying other locations, may still be a bottleneck to using the CRISPR/Cas9 system, because the gRNA may also bind to locations with slightly different DNA sequences. This makes the process of finding all potential off-target sites (genome locations that are sufficiently similar to the gRNA targeting sequence) computationally expensive, especially when one allows more differences (i.e., Hamming distance) from the reference sequence.

The time complexity of searching for exact matches can be expressed as O (n*l*L), where n is the number of gRNA targeting sequences to be searched, l is the length of the query sequence (or target sequence), and L is the length of the reference genome. The time complexity may be worsened when differences (i.e., Hamming distances) are allowed. There are several local off-target search tools (running on local workstations), but the performance may not be acceptable, even with the help of GPUs. For example, it may take days to search for potential off-target sites when only allowing several mis-matches.

SUMMARY

Embodiments according to the present inventive concept can provide methods, circuits, systems, and articles of manufacture for searching a reference sequence for a target sequence within a specified difference. Pursuant to these embodiments, a method of operating a finite state machine circuit can be provided by determining if a target sequence of characters included in a string of reference characters occurs within a specified distance using states indicated by the finite state machine circuit to indicate a number of character mis-matches between the target sequence of characters and a respective sequence of characters within the string of reference characters.

DETAILED DESCRIPTION OF EMBODIMENTS ACCORDING TO THE INVENTION

Figure 1A:
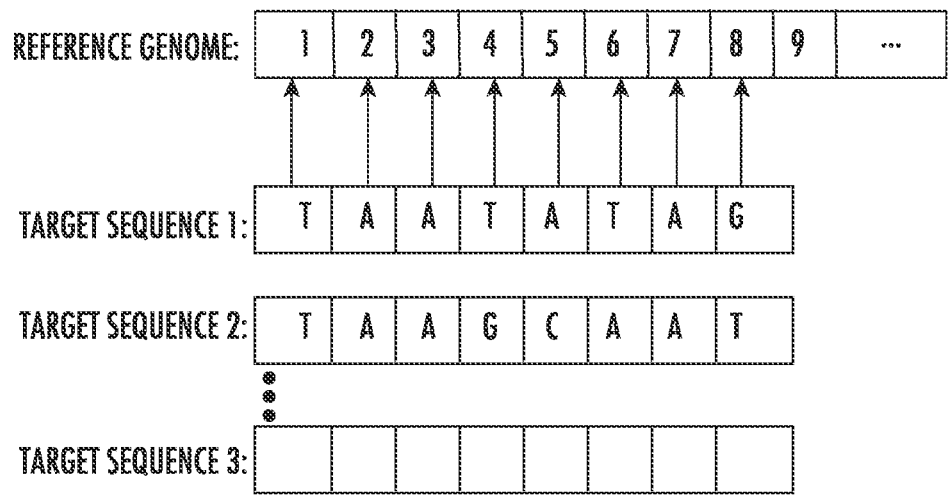
FIG. 1A is a schematic representation of a reference genome represented by characters compared to a plurality of different target sequences of characters in some embodiments according to the invention.

Advantages and features of the present disclosure and methods of accomplishing the same may be understood more readily by reference to the following detailed description of preferred embodiments and the accompanying drawings. The present disclosure may, however, be embodied in many different forms and should not be construed as being limited to the embodiments set forth herein. Rather, these embodiments are provided so that this disclosure will be thorough and complete and will fully convey the concept of the present disclosure to those skilled in the art, and the present disclosure will only be defined by the appended claims. Like reference numerals refer to like elements throughout the specification.

As appreciated the present inventors, spatial architectures, such as a field programmable gate array (FPGA) and Micron's Automata Processor (AP), may provide a performance improvement in searching for target sequences within a reference genome while also allowing for a specified number of mis-matches between the target sequence and the reference genome to identify off-target sites within the reference genome. For example, in some embodiments according to the invention, the search for a target sequence within the reference genome (and variations on the target sequence within a specified difference) can be provided by a finite state machine circuit which provides transitions between states based on the result of a comparison between one of the characters in the target sequence and a corresponding one of the characters in the reference genome. For example, in comparing one of the characters in the target sequence to a corresponding one of the characters in the reference genome, the finite state machine circuit can transition from a first state to a second state if the two characters match whereas the finite state machine circuit may transition from the first state to a third state if the two characters do not match (i.e., mis-match). It will be understood that the specified difference can be provided by a Hamming distance, edit distance (Levenshtein distance) or other specially defined distances such as only allowing insertions, deletion, any combination of insertions, deletions and substitutions, or assigning match/mismatch at certain position.

As further appreciated by the present inventors, using different states to capture the result of the comparison between the target sequence characters and reference genome characters can preserve the number of mis-matches so that the finite state machine circuit can more quickly indicate whether the specified difference for the comparison has been exceeded. Moreover, using the finite state machine circuit to compare the target sequence characters to the reference genome characters can be done, for example, on every clock edge used to drive the finite state machine circuit thereby reducing the search time. Furthermore, a custom finite state machine circuit can be generated for each target sequence that is to be compared to the reference genome. In this way each of the customized finite state machine circuits can be run in parallel against the reference genome so that multiple target sequences can be checked simultaneously, which can reduce the search time for off-target sites of all target sequences.

In still further embodiments according to the invention, a cross-correlation circuit can be used to compare the target sequence characters to the reference genome characters in parallel (i.e., without the use of finite states). It will be understood that the term "search circuit" can be used herein to describe a circuit that uses either a finite state machine circuit or a cross-correlation circuit to search for off-target sites within the reference genome.

FIG. 1A is a schematic representation of a sequence of characters representing a reference genome as well as a sequence of characters included in a number of target sequences to be searched for in the reference genome in some embodiments according to the invention. According to FIG. 1A, the reference genome includes a large number of characters which represent base pairs known to be included in the particular sequence of the genome. As further shown in FIG. 1A, each of the target sequences (1-N) includes a specific sequence of base pairs which are to be searched for within the reference genome sequence.

According to FIG. 1A, the characters (for example including eight characters) in each target sequence are compared to eight characters of the reference genome. It will be understood that in the example shown in FIG. 1A, each of the characters in each of the target sequences is compared to a corresponding one of the characters representing the reference genome sequence. For example, the character T, as the first character in the target sequence 1, is compared to the first character found in position one of the reference genome. Furthermore, each of the characters in the target sequence 1 is compared against the corresponding one of the characters included in the reference genome at the particular position. For example, the first character T in the target sequence 1 is compared against the character found in the first position of the reference genome whereas the second character A of the target sequence 1 is compared against the second character in the reference genome and so on for all of the characters in the target sequence 1. It will be understood that this process can be carried out for each of the target sequences 1-N in FIG. 1A, where each target sequence is evaluated for the number of off-target sites in the reference genome for that particular target sequence.

It will be understood that although FIG. 1A illustrates the comparison of each of the characters to a corresponding one of the characters in the reference genome, the search provided herein by the finite state machine circuit may stop the search when a specified difference is exceeded during the search. In other words, even though the FIG. 1A illustrates the comparison of each of the characters in the target sequence against each of the corresponding one of the characters in the reference genome, the actual search carried out by the finite state machine circuit may perform fewer compares.

Although the operations herein are described relative to the comparison of a target sequence of characters to characters within a reference genome, these types of operations may be utilized in other applications. For example, in some embodiments according to the invention, the target sequence may represent any arbitrary subsequence of characters located within a long string of characters which are searched for similar sequences. Still further, in some embodiments according to the invention, the operations described herein can be carried out in entirely in hardware, entirely in software, or using a combination of hardware and software.

Figure 1B:
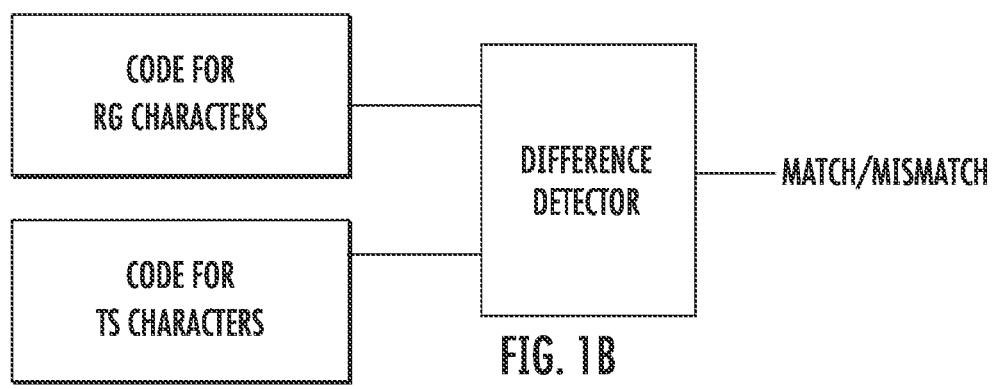
FIG. 1B is a schematic representation of a comparison circuit configured to compare codes representing the reference genome characters to codes representing corresponding ones of the target sequence characters to indicate a match/mis-match in some embodiments according to the invention.

FIG. 1B is a schematic representation of a circuit that can be utilized to compare codes that represent the reference genome characters to codes that represent the target sequence characters. According to FIG. 1B, the codes for each of the characters is compared using an XOR function which indicates whether the codes are equal or unequal (i.e., match or mis-match). It will understand that the representation shown in FIG. 1B is for illustrative purposes and is not necessarily literal representation of the circuits used for the comparison. Rather, FIG. 1B illustrates that each of the characters in the reference genome is compared to the target sequence character that corresponds to the reference genome character the result of which can be captured by the particular state transition that is provided by operation on the finite state machine circuit in some embodiments according to the invention.

Figure 1C:
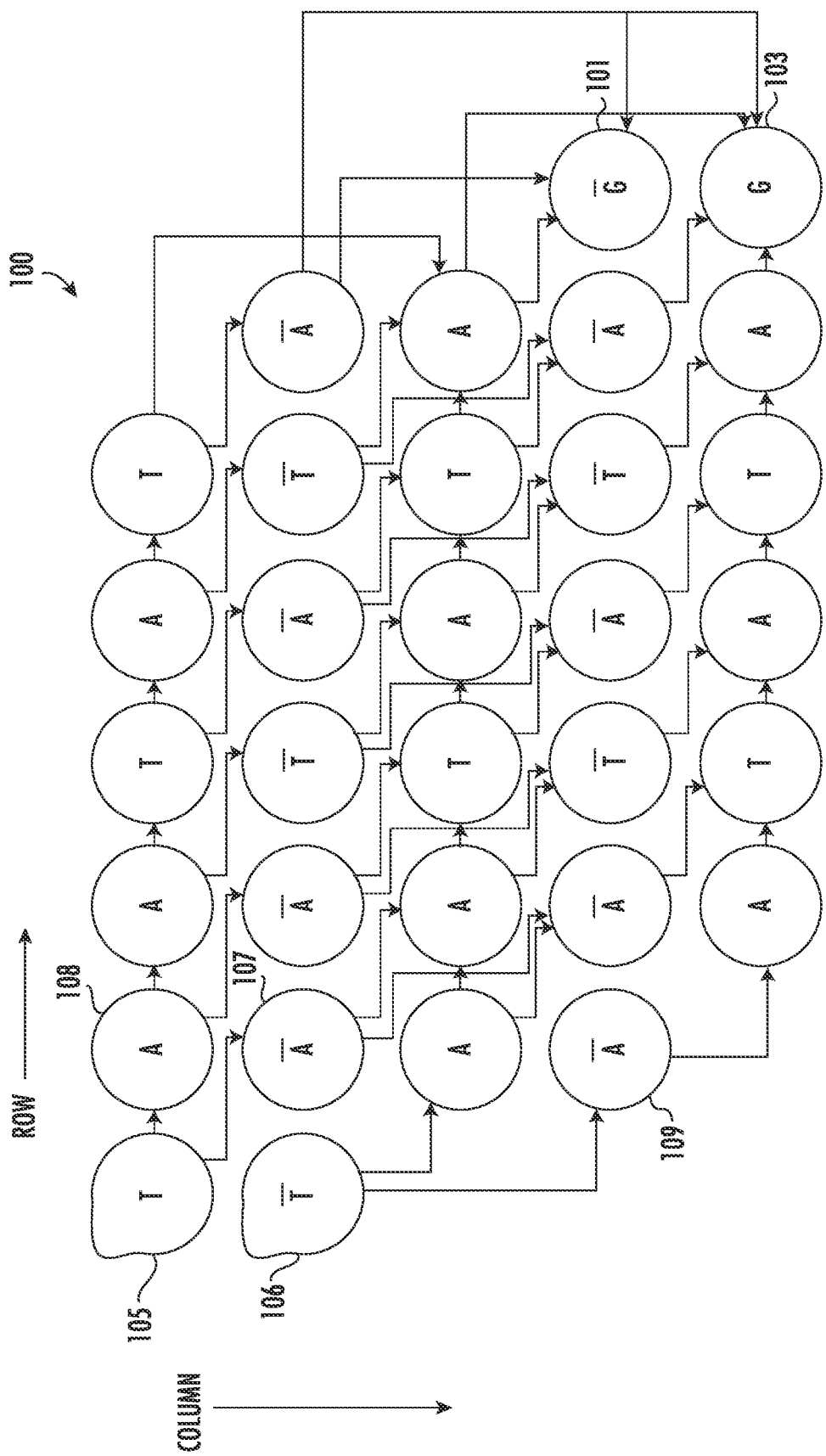
FIG. 1C is a schematic representation of states generated by a finite state machine circuit in carrying out the comparison illustrated in FIG. 1A to indicate a match/mis-match between each of the reference genome characters and respective ones of the target sequence characters within a Hamming distance of 2 in some embodiments according to the invention.

FIG. 1C is a schematic representation of states generated by a finite state machine circuit 100 in carrying out the comparison illustrated in FIG. 1A to indicate a match/mismatch between each of the reference genome characters and respective ones with target sequence characters within a specified difference of two in some embodiments according to the invention. According to FIG. 1C, the states provided by operation of the finite state machine circuit 100 are organized in an array of rows and columns where each column represents a comparison between reference genome characters and characters in the target sequence. For example using the target sequence of FIG. 1A, the first column shown in FIG. 1C of the finite state machine circuit 100 illustrates the comparison of the character T in the target sequence to a corresponding one of the characters in the reference genome sequence. Furthermore, each of the columns corresponds to one target sequence character to be compared to a reference genome character.

As further shown in FIG. 1C, each of the states corresponds to a state transition circuit 105. It will be understood that each of the state transition circuits 105 can be provided by a sequential logic circuit (such as a flip flop or latch) having combinatorial logic gates provided to the input of the sequential logic circuit and that is driven by a common clock within the finite state machine circuit 100. Each of the state transition circuits 105 can be connected to other ones of the state transition circuits in the array to capture the result of the comparison of the target sequence character corresponding to a respective one of the characters in the reference genome. For example, the finite state machine circuit 100 can begin operation by comparing the target sequence character T to the first character found within the reference genome. If the character found in the reference genome at position 1 is a T, the state machine begins operation with state transition circuit 105 of the array. Alternatively, if the first character found in the reference genome sequence is not T, the operation of the state machine 100 begins in the state transition circuit 106.

On the next clock edge the state machine circuit 100 transitions from the starting state to the next state based on the result of the comparison of the second character in the target sequence to the character found at the second position of the reference genome. For example, if the first character in the reference genome was a T (above), the state machine circuit 100 will transition to the state transition circuit 108 shown to the immediate right (i.e., in the same row) if the second character in the target sequence is equal to the character found in the second position of the reference genome (i.e., A). If, however, the second character in the reference genome is not A, the state machine circuit 100 transitions from state transition circuit 105 to state transition circuit 107. Accordingly, the transition to the second row by the state machine circuit 100 captures the mis-match between the second characters, which is preserved during subsequent transitions of the state machine.

It will be understood that the structure shown in FIG. 1C of the state machine 100 illustrates that the finite state machine 100 functions to compare the target sequence characters to the reference genome characters in the first window until the difference of two is exceeded. For example, the structure shown in FIG. 1C illustrates that the comparison between the target sequence characters and the corresponding reference genome characters is considered to qualify as an off-target site if the state machine circuit 100 transitions through the states shown in FIG. 1C to terminate in the states 101 or 103 shown on the lower right hand portion of the array. Accordingly, if the state machine circuit 100 operates to reach either of the states 101 or 103, the state machine circuit 100 reports the particular target sequence of characters used to search the reference genome as a potential off-target site.

As shown in FIG. 1C, the states shown in the first row are utilized if the first six characters of the target sequence match the first six characters of the reference genome. In other words, transitions of the state machine along the same row indicate a match in the corresponding characters of the target sequence and the reference genome. Transitions in the column direction, however, indicate a mis-match between characters. For example, transitioning from state transition circuit 105 to state transition circuit 107 captures the fact that the character A at the second position of the target sequence did not match the character found at the second position of the reference genome. The transition to the second row indicates that a mis-match occurred and therefore the difference distance is increased to 1, whereas when the transitions occur in the row direction, the difference distance is unchanged.

The number of rows within the array in FIG. 1C specifies that the difference distance of the state machine circuit 100 reports the target sequence as being an off-target site if the difference distance between the target sequence and the reference genome is 2 or less. In other words, if the difference distance between the target sequence and the reference genome is 3 or more, the state machine circuit may cease operation. Although not shown, it will be understood that other states may be used by the state machine circuit 100 to represent the termination of the finite state machine circuit 100 where the specified difference distance encoded by the array is exceeded. Accordingly, those states can be used to report that the particular target sequence is not an off-target site.

Figure 1D:
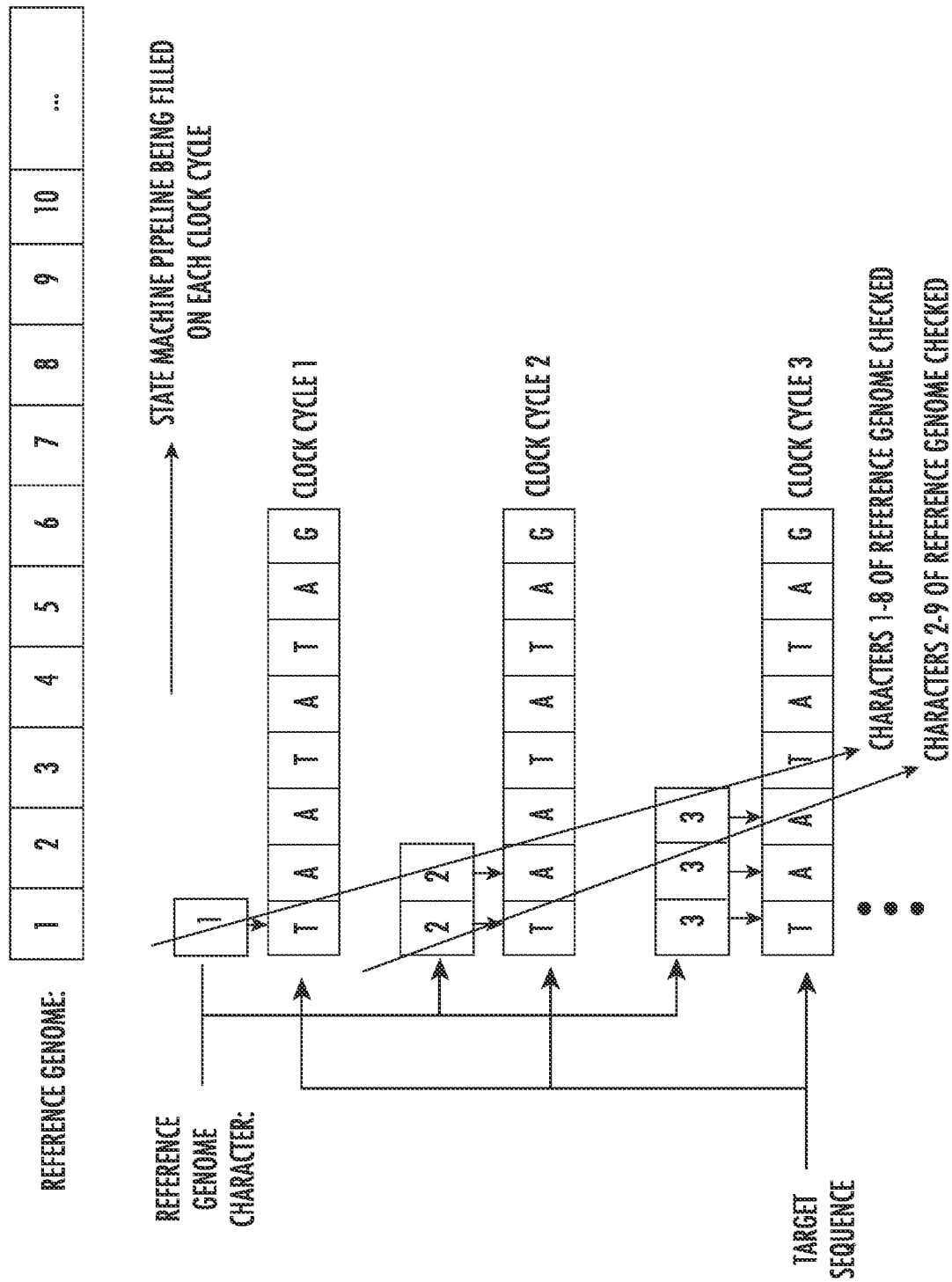
FIG. 1D is a schematic representation of operations of the finite state machine circuit of FIG. 1C used to compare the reference genome characters to the target sequence characters on a per clock cycle basis in some embodiments according to the invention.

FIG. 1D is a schematic representation of operations of the finite state machine circuit of FIG. 1C used to compare the reference genome characters to the target sequence characters on a per clock cycle basis in some embodiments according to the invention. According to FIG. 1D, a comparison is performed between the N characters of the target sequence and every sequence of characters within the reference that includes N characters. For example, the state machine compares the 8 characters in the target sequence to: characters 1-8 of the reference genome, characters 2-9 of the reference genome, characters 3-10, and so on up to the last characters of the reference genome. It will be understood, however, this is an example and embodiments according to the inventive concept are not limited to eight 8 characters (ie., any number of characters can be used).

As further shown in FIG. 1D, each of the different ranges of reference genome characters can be compared to target sequence by pipelining the operation of the state machine. In particular, on the first clock cycle the first reference genome character can be provided to the state machine, followed by providing the second reference genome character to the state machine for comparison to the first and second characters of the target sequence. On the next clock cycle (3) the third character of the reference genome is provided for comparison with the first three characters of the target sequence. This type of operation can be continued until the entire reference genome has been processed by the finite state machine pipeline. Moreover, once the finite state machine pipeline is full, each subsequent clock cycle can produce a report on whether that particular range of reference genome characters is an off-target site.

Figure 2:
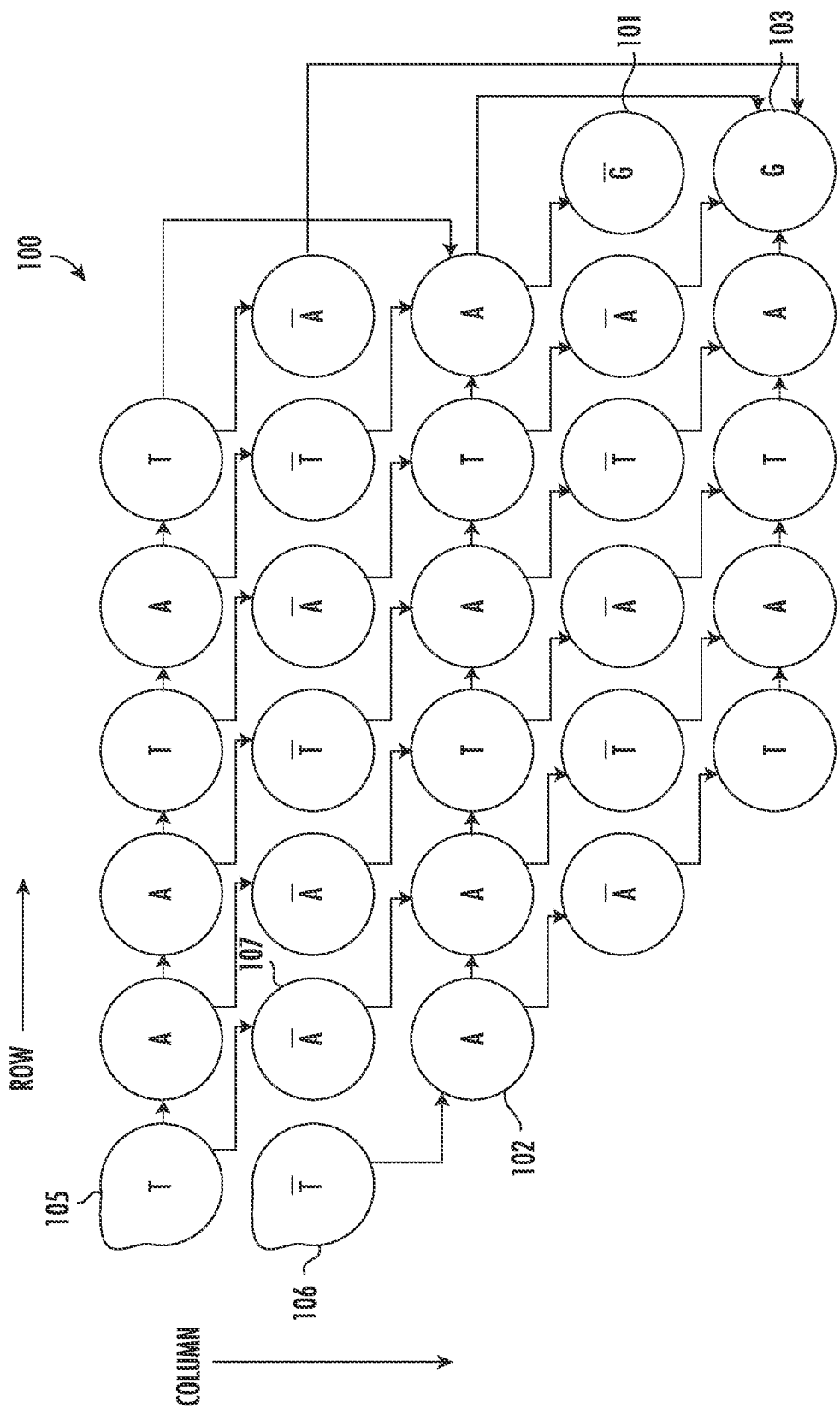
FIG. 2 is a schematic representation of states generated by a finite state machine circuit used to compare the reference genome characters to the target sequence characters as shown in FIG. 1A to within a Hamming distance of 2 with no consecutive mis-matches of characters permitted in some embodiments according to the invention.

FIG. 2 is a schematic representation of states generated by the finite state machine circuit 100 in carrying out the comparison illustrated in FIG. 1A to indicate a match/mis-match in the comparison of each of the reference genome characters to respective ones with target sequence characters within a specified Hamming distance of two with the additional condition that two consecutive mis-matched characters are not allowed in some embodiments according to the invention.

According to FIG. 2, the states provided by operation of the finite state machine circuit 100 are organized in an array of rows and columns where each column represents a comparison to a corresponding one of the characters in the target sequence. For example using the target sequence of FIG. 1A, the first column shown in FIG. 2 of the finite state machine circuit 100 illustrates the comparison of the first character T in the target sequence to a corresponding one of the characters in the reference genome sequence. Furthermore, each of the columns corresponds to one of the target sequence characters to be compared to the reference genome characters. As further shown in FIG. 2, each of the states corresponds to a state transition circuit.

The operation of the finite state machine circuit 100 in FIG. 2 is generally the same as that described above in reference to FIG. 1C. The allowed transitions between the states, however, reflect the structural difference between the state machine circuits of FIG. 1C and FIG. 2. Specifically, while the finite state machine circuit 100 does allow for two mis-matches between characters, the finite state machine circuit 100 of FIG. 2 does not allow two consecutive character mis-matches. For example, if the finite state machine circuit of FIG. 2 enters state transition circuit 106 (indicating a mis-match in the first characters) the only transition allowed out of state transition circuit 106 is to state transition circuit 102. The finite state machine circuit 100 of FIG. 2 does not, however, provide a transition to a state that is equivalent to the finite state transition circuit 109 shown in FIG. 1C (i.e, state 109 captures two consecutive mis-matches, which is not allowed in the architecture of the finite state machine circuit 100 of FIG. 2). Accordingly, the operation of the finite state machine circuit 100 in FIG. 2 will stop.

Figure 3:
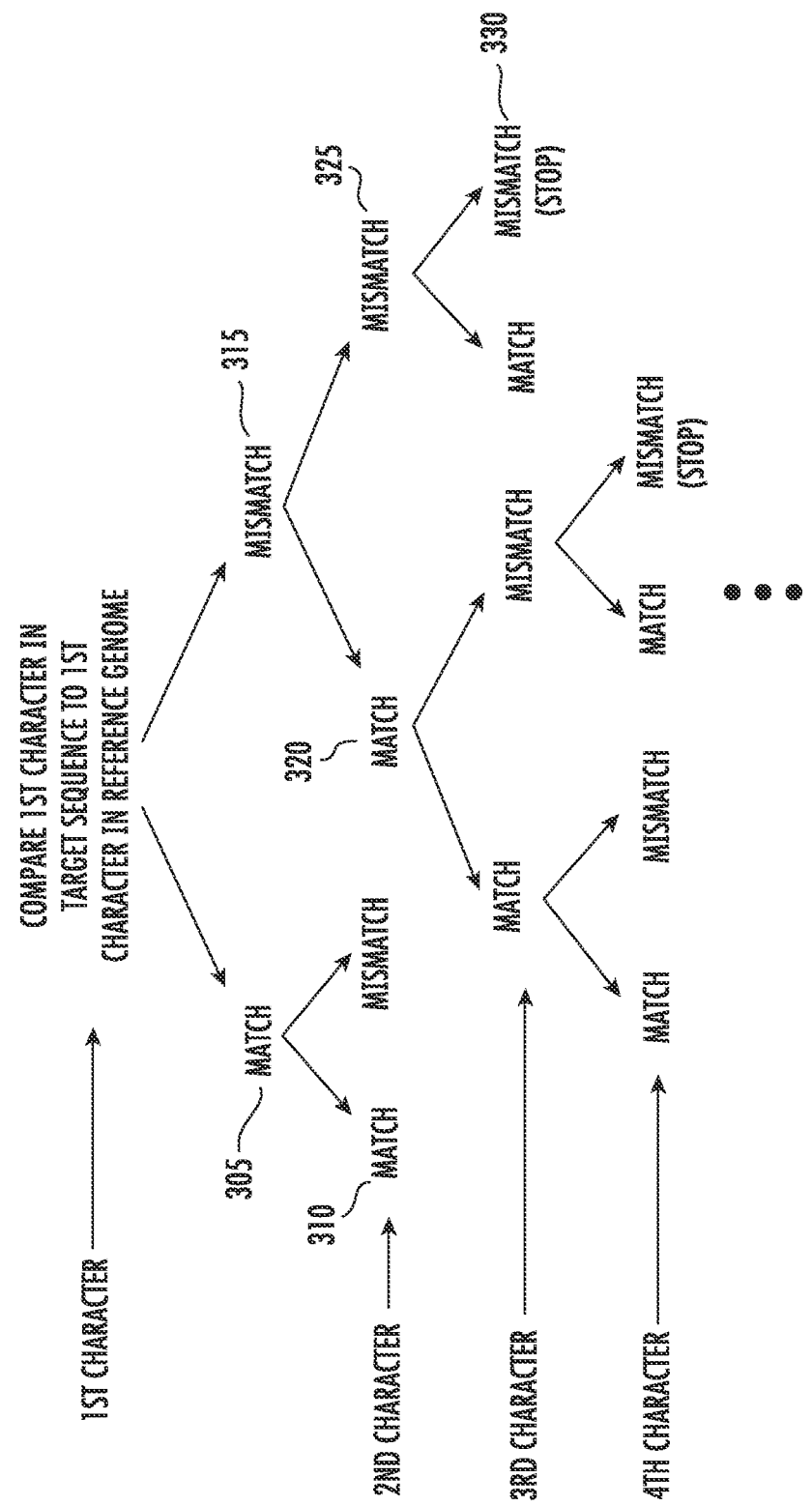
FIG. 3 is a schematic representation of the search provided using the finite state machine circuit in FIG. 1C illustrating the state transitions in response to the character comparisons in view of the Hamming distance of 2 in some embodiments according to the invention.

FIG. 3 is a schematic representation of the search provided using the finite state machine circuit shown in FIG. 1C illustrating the state transitions in response to character comparisons in view of the specified Hamming distance in some embodiments according to the invention. According to FIG. 3, operations begin when the first character of the target sequence is compared to the first character of the reference genome. If the first character of the target sequence matches the first character of the reference genome operations can continue at step 305 whereupon the second character of the target sequence is compared to the second character of the reference genome (step 310).

If, however, the first character in the target sequence does not match the first character in the reference genome, operations continue at step 315 where the second character of the target sequence is compared to the second character of the reference genome. If these character match operations continue at step 320 whereas if the characters mis-match operations continue at step 325. If operations reach step 325 the finite state machine circuit captures that two of the characters to this point have mis-matched one another, therefore if the next character of the target sequence mis-matches the next character of the reference genome at step 330 operations stop as the finite state machine circuit has detected that the target sequence in the reference genome include at least three mis-matching characters (i.e., exceeds the Hamming distance).

Figure 4:
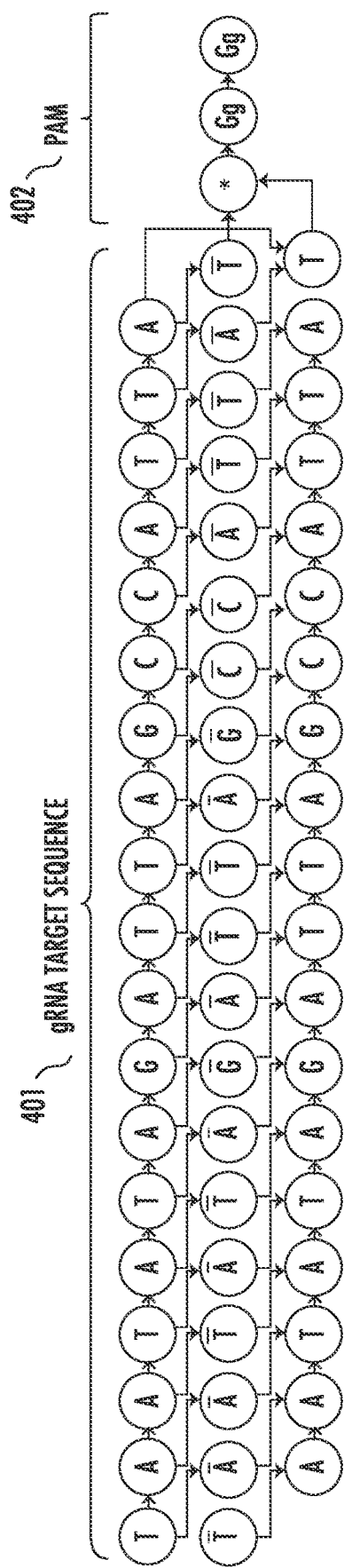
FIG. 4 is a schematic representation of states generated by a first portion of a finite state machine circuit configured to compare a gRNA target sequence to a reference genome sequence, coupled to a second portion of the finite state machine circuit configured to compare a PAM sequence to the reference genome sequence in some embodiments according to the invention.

FIG. 4 is a schematic representation of states of a first portion of a finite state machine circuit configured to compare sequences of a gRNA target sequence, coupled to a second portion of the finite state machine circuit configured to compare sequences of a PAM sequence, to the reference genome in some embodiments according to the invention. According to FIG. 4, the first portion of the finite state machine circuit 401 compares characters in the reference genome sequence (TAATATAGATTAGCCATTA, SEQ ID NO:4 and AATATAGATTAGCCATTAT, SEQ ID NO:5) to the specified gRNA target sequence that is encoded in the state machine 401 (TAATATAGATTAGCCATTAT, SEQ ID NO:1).

As shown in FIG. 4, the first portion of the finite state machine circuit 401 allows for a single mis-match in the comparison of the reference genome sequence to the target sequence (i.e., a difference of one). As further shown in FIG. 4, the first portion of the finite state machine circuit 401 is coupled to a second portion of the finite state machine circuit 402 that is configured to compare the target sequence of * G G to the PAM sequence within the reference genome sequence (where * can represent any character). Accordingly, the second portion of the finite state machine circuit 402 allows for any character to be detected in the first character of the PAM sequence whereas the remaining characters must both be G in order for the match to occur. In other words, the second portion of the finite state machine circuit 402 does not allow for any mis-matches in characters beyond the wildcard representation of the first character in the PAM sequence.

Figure 5:
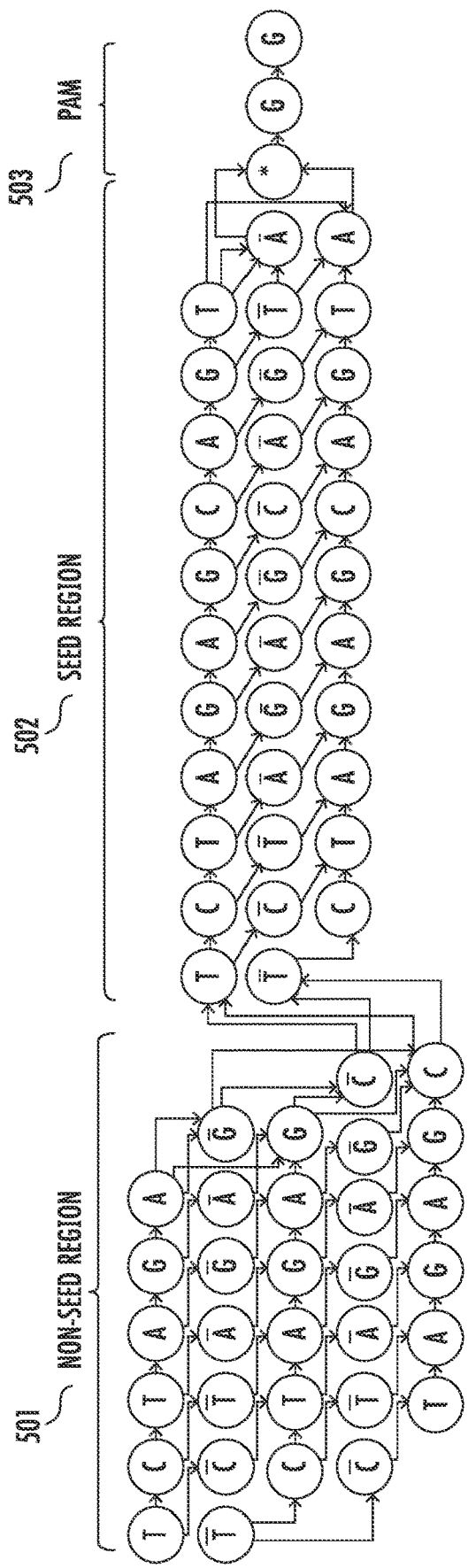
FIG. 5 is a schematic representation of a first portion of a finite state machine circuit configured to compare sequences of a non-seed region of a gRNA sequence to the reference genome sequence, coupled to a second portion of the finite state machine circuit configured to compare sequences of a seed region of the gRNA sequence to the reference genome sequence, coupled to a third portion of the finite state machine circuit configured to compare a PAM sequence to the reference genome sequence in some embodiments according to the invention.

FIG. 5 is a schematic representation of a first portion of the finite state machine circuit 501 that is configured to compare sequences within a non-seed region of the gRNA target sequence to the reference genome sequence, coupled to a second portion of the finite state machine circuit 502 that is configured to compare sequences within a seed region of the gRNA target sequence to the reference genome sequence, coupled to a third portion of the finite state machine circuit 503 that is configured to compare sequences of a PAM sequence to the reference genome sequence in some embodiments according to the invention. According to FIG. 5, the first portion of the finite state machine circuit 501 compares the sequence TCTAGAGC, that are characters within a non-seed region of the gRNA target sequence, to the reference genome sequence while allowing for a difference distance of two where no two mis-matches are allowed to be consecutive. The second portion of the finite state machine circuit 502 is coupled in series with the first portion of the finite state machine circuit 501, where the second portion of the finite state machine circuit 502 compares the sequence TCTAGAGCAGTA (SEQ ID NO:2), that are characters within a seed region of the gRNA target sequence, to the reference genome sequence (TCTAGAGCAGT, SEQ ID NO:6 and CTAGAGCAGTA, SEQ ID NO:7). Moreover, the second portion of the finite state machine circuit 502 is configured to allow for a single mis-match between the target sequence characters and the reference genome sequence characters. Accordingly, different number of mis-matches can be selected for seed and non-seed regions. The a third portion of the finite state machine circuit 503 is coupled to the output of the second portion of the finite state machine circuit 502 and has the same configuration state machine 402 described above in reference to FIG. 4.

Figure 6:
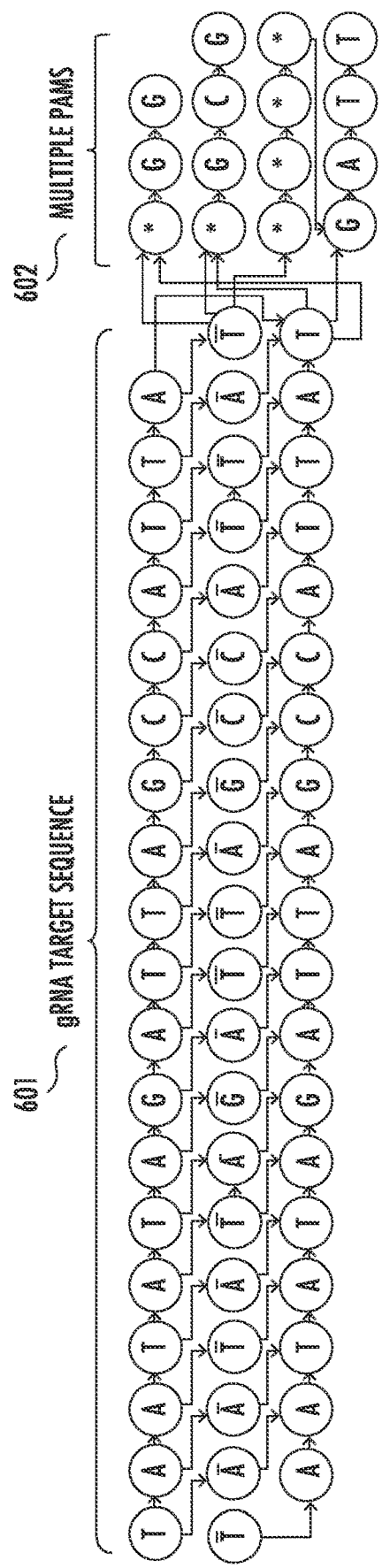
FIG. 6 is a schematic representation of a first portion of a finite state machine circuit configured to compare a gRNA target sequence to the reference genome sequence, coupled to a second portion of the finite state machine circuit that is configured to compare multiple PAM target sequences to the reference genome sequence in some embodiments according to the invention.

FIG. 6 is a schematic representation of a first portion of a finite state machine circuit 601 configured to compare a gRNA target sequence to the reference genome sequence, coupled to a second portion of the finite state machine circuit 602 that is configured to compare multiple PAM sequences to the reference genome sequence in some embodiments according to the invention. According to FIG. 6, the first portion of the finite state machine circuit 601 is configured to compare the target sequence TAATATAGATTAGCCAT-TAT (SEQ ID NO:1) to corresponding ones of the characters included in the reference genome sequence (TAATATA-GATTAGCCATTA, SEQ ID NO:4 and AATATAGATT-AGCCATTAT, SEQ ID NO:5). The last column of the circuit 601 is connected to the input of the second portion of the finite state machine circuit 602 which is configured to compare multiple different PAM sequences.

Figure 7:
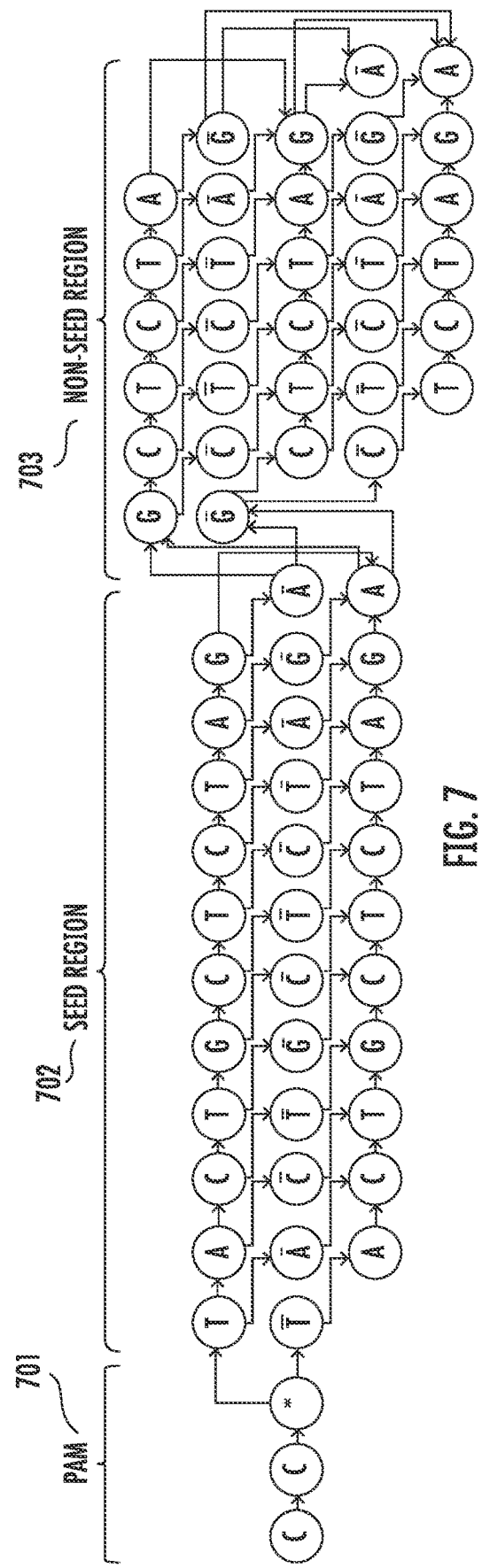
FIG. 7 is a schematic representation of a first portion of a finite state machine circuit that is configured to compare a sequence complementary to a PAM sequence to the reference genome sequence, coupled to a second portion of the finite state machine circuit that is configured to compare a sequence complementary to sequences of a seed region of a gRNA target sequence to the reference genome sequence, coupled to a third portion of the finite state machine circuit that is configured to compare a sequence complementary to sequences of a non-seed region of the gRNA target sequence to the reference genome sequence in some embodiments according to the invention.

FIG. 7 is a schematic representation of a first portion of a finite state machine circuit 701 that is configured to compare a sequence complementary to a PAM target sequence to the reference genome sequence, coupled to a second finite state machine circuit 702 that is configured to compare a sequence complementary to sequences within a seed region of a gRNA target sequence (TACTGCTCTAGA, SEQ ID NO:3) to the reference genome sequence (TACTGCTCTAG, SEQ ID NO:8 and ACTGCTCTAGA, SEQ ID NO:9), coupled to a third portion of the finite state machine circuit 703 that is configured to compare a sequence complementary to sequences within a non-seed region of the gRNA target sequence to the reference genome sequence in some embodiments according to the invention. According to FIG. 7, the first, second, and third portions of the finite state machine circuits 701-703 are coupled in series with one another and represent the inverse of the finite state machine structure shown in FIG. 5 and therefore can be used to search for the complimentary strand of the reference genome sequence shown in FIG. 5.

Figure 8:
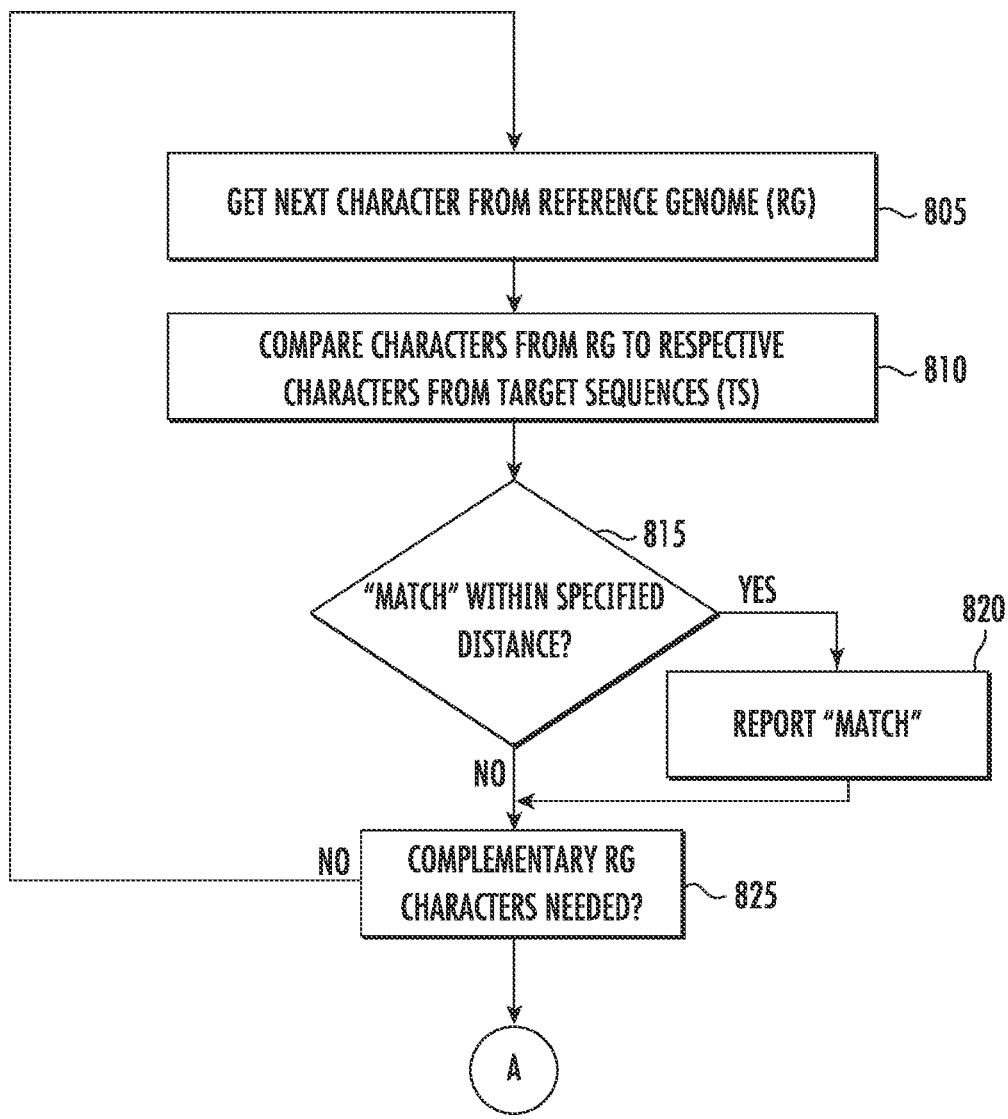
FIG. 8 is a flowchart that illustrates operations of a system that includes the finite state machine circuit shown in FIG. 1C upon completion of comparison of the target sequence to the reference genome sequence in some embodiments according to the invention.

FIG. 8 is a flowchart that illustrates operations of a system that includes the finite state machine circuit shown in FIG. 1C upon completion of comparison of the target sequence to the reference genome sequence in some embodiments according to the invention. According to FIG. 8, operations can begin at block 805 wherein the next reference character from the reference genome is fetched and compared to respective characters from the target sequence (block 810). If the characters of the reference genome match those of the target sequence within the specified difference distance (block 815) the finite state machine circuit reports a match within the difference distance (block 820) indicating that the target sequence represents an off target site within the reference genome whereupon operations can continue at block 805 wherein the compliment of the reference genome characters can be compared relative to the target sequence wherein the same operations outlined above blocks 805-820 (and shown as a state machine in FIG. 7) can be repeated for the complimentary sequence.

Figure 9:
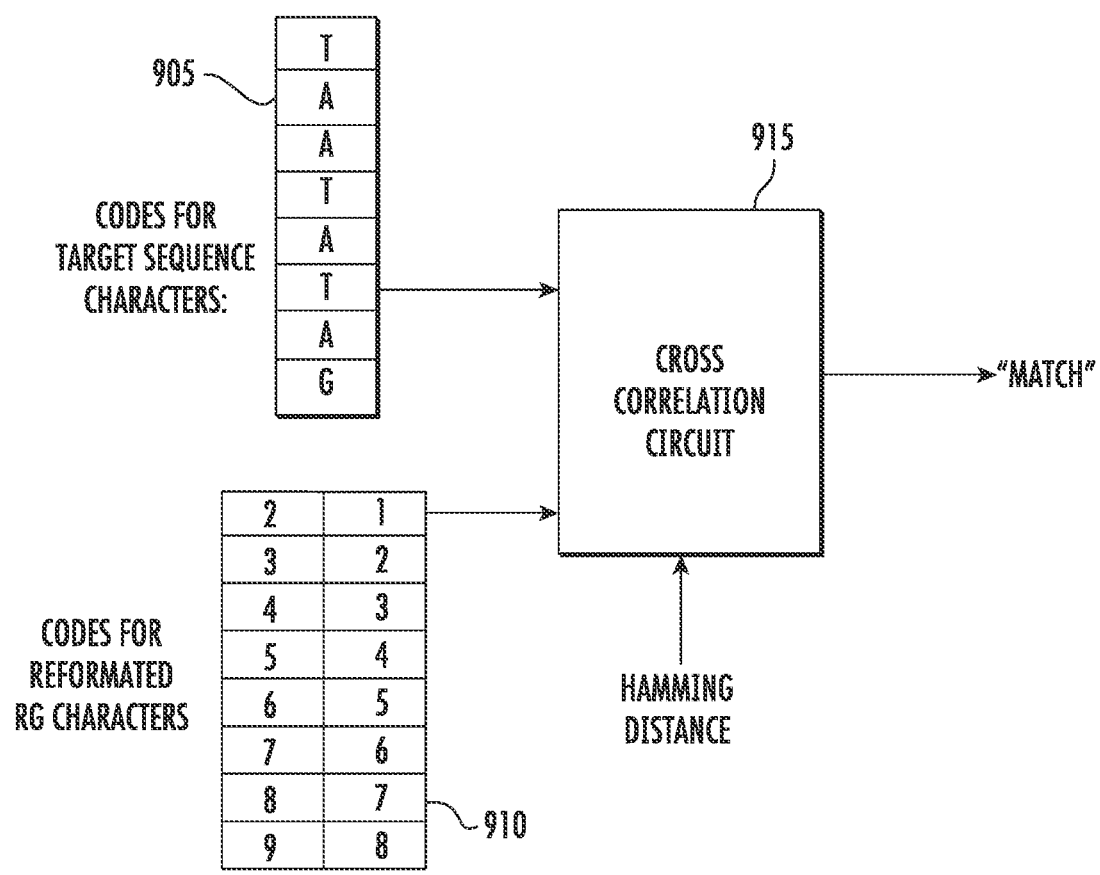
FIG. 9 is a schematic representation of a cross-correlation circuit configured to compare codes corresponding to the target sequence to codes corresponding to the reference genome sequence to determine a match within a Hamming distance thereof in some embodiments according to the invention.

FIG. 9 is a schematic representation of a cross-correlation system 900 configured to compare codes 905 corresponding to the target sequence to codes 910 corresponding to the reference genome sequence using a cross-correlation circuit 915 to determine a match within a specified Hamming distance. According to FIG. 9, the codes 905 representing the target sequence characters described above in reference to FIG. 1A can be compared to the reformatted codes 910 for the reference genome characters 1-8 using the cross-correlation circuit 915.

In particular, the codes 905 representing the target sequence characters can be compared in parallel to respective codes 910 for the reference genome sequence shown in FIG. 9. The characters of the reference genome can be reformatted to be in parallel with one another (i.e., 1-8 are in parallel with one another rather than in sequence with one another as shown in FIG. 1A) which are compared to the respective codes 905 of the target sequence characters. The cross correlation circuit 915 can therefore determine a comparison between each of the codes 905 for the target sequence characters to the codes 910 for the reference genome characters in parallel with one another within the specified Hamming distance so that the cross correlation circuit can provide a match or mis-match rather than as series of sequential operations.

Figure 10:
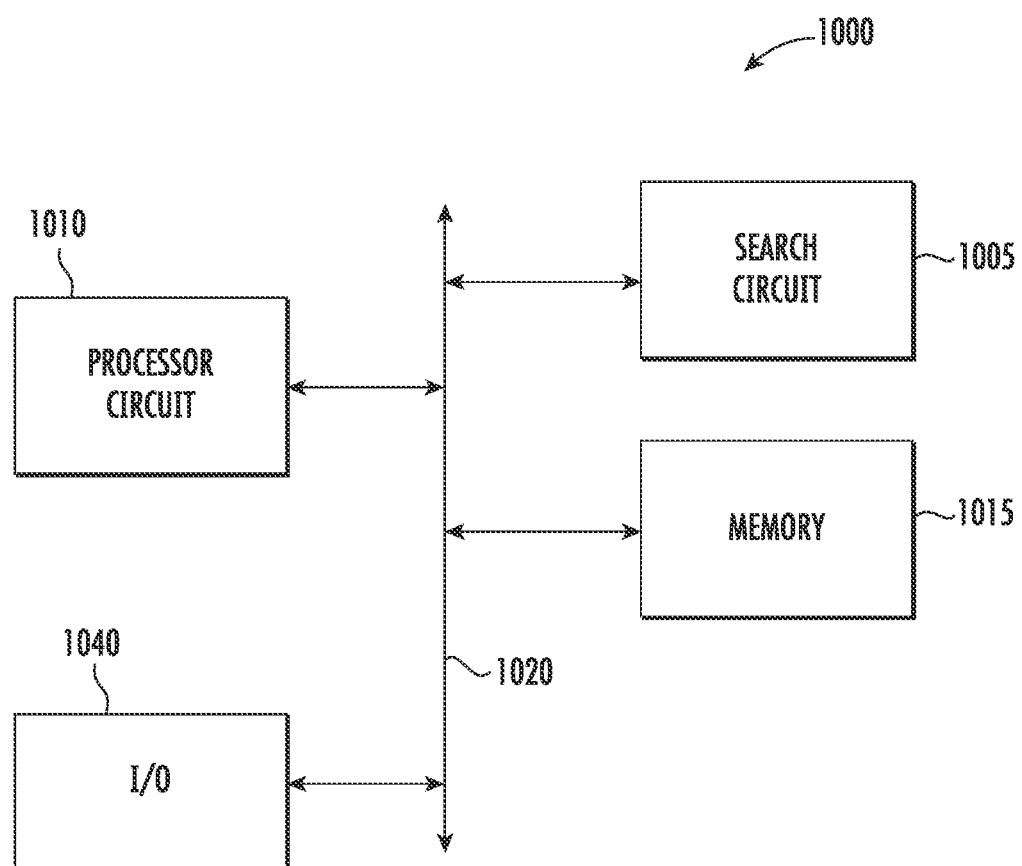
FIG. 10 is a block diagram illustrating a system in which a search circuit (finite state machine circuit or cross correlation circuit) may be employed in some embodiments according to the invention.

FIG. 10 illustrates a block diagram showing an example architecture of a system 1000 in which a search circuit 1005 may be implemented in some embodiments according to the invention. The system 1000 can include one or more processor circuits 1010 and a memory 1015 coupled to an interconnect 1020. The interconnect 1020 may be an abstraction that represents any one or more separate physical buses, point to point connections, or both connected by appropriate bridges, adapters, or controllers. The interconnect 1020, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The processor circuit 1010 may be the central processing unit (CPU) of the system 1000 and, thus, control the overall operation of the system. In certain embodiments, the processor circuit 1010 can accomplish this by executing software or firmware stored in memory 1015. The processor circuit 1010 may be, or may include, one or more programmable general purpose or special-purpose microprocessors, digital signal processors (DSPs), programmable controllers, application specific integrated circuits (ASICs), programmable logic devices (PLDs), field-programmable gate arrays (FPGAs), trusted platform modules (TPMs), or a combination of such or similar devices.

The memory 1015 can be (or include) the main memory of the system 1000. The memory 1015 represents any form of random access memory (RAM), read-only memory (ROM), flash memory, or the like, or a combination of such devices. In use, the memory 1015 may contain code containing instructions according to the techniques disclosed herein. For example, the code may represent the structure of the search circuit 1005 when the processor circuit executes the code. The code stored in memory 1015 may be implemented as software and/or firmware to program the processor circuit 1010 to carry out actions described above in addition to providing the structure of the search circuit. In certain embodiments, such software or firmware may be initially provided to the system 1000 by downloading it from a remote system via the I/O adapter 1040, which can provide the system 1000 with the ability to communicate with remote devices over a network and may be a wireless connection or a wired connection (such as an Ethernet adapter, a Bluetooth adapter, etc.)

Embodiments of the present disclosure were described herein with reference to the accompanying drawings. Other embodiments may take many different forms and should not be construed as limited to the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the various embodiments described herein. As used herein, the term "and/or" includes any and all combinations of one or more of the associated listed items.

The terminology used herein is for the purpose of describing particular embodiments only and is not intended to be limiting to other embodiments. As used herein, the singular forms "a", "an" and "the" are intended to include the plural forms as well, unless the context clearly indicates otherwise. It will be further understood that the terms "comprises," "comprising," "includes" and/or "including", "have" and/or "having" when used herein, specify the presence of stated features, integers, steps, operations, elements, and/or components, but do not preclude the presence or addition of one or more other features, integers, steps, operations, elements, components, and/or groups thereof. Elements described as being "to" perform functions, acts and/or operations may be configured to or other structured to do so.

Unless otherwise defined, all terms (including technical and scientific terms) used herein have the same meaning as commonly understood by one of ordinary skill in the art to which various embodiments described herein belong. It will be further understood that terms used herein should be interpreted as having a meaning that is consistent with their meaning in the context of this specification and the relevant art and will not be interpreted in an idealized or overly formal sense unless expressly so defined herein.

As will be appreciated by one of skill in the art, various embodiments described herein may be embodied as a method, data processing system, and/or computer program product. Furthermore, embodiments may take the form of a computer program product on a tangible computer readable storage medium having computer program code embodied in the medium that can be executed by a computer.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wired, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages, such as a programming language for a FPGA, Verilog, System Verilog, Hardware Description language (HDL), and VHDL. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

Some embodiments are described herein with reference to flowchart illustrations and/or block diagrams of methods, systems and computer program products according to embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall support claims to any such combination or subcombination.

What is claimed:

1. A method of operating a finite state machine on a system comprising a memory and at least one processor coupled to the memory and configured to perform the method, the method comprising:

determining if a target sequence of characters is included in a string within a reference sequence of characters using states indicated by the finite state machine to indicate a number of character mismatches between the target sequence of characters and the string within the reference sequence of characters, wherein the target sequence of characters and the string within the reference sequence of characters are nucleic acid sequences, wherein the reference sequence of characters comprise a genome, and wherein determining comprises:

comparing, in a first state of the finite state machine, one of the target sequence of characters to a respective one of the reference sequence of characters;

transitioning from the first state to a second state of the finite state machine responsive to a match between the one of the target sequence of characters and the respective one of the reference sequence of characters when in the first state and maintaining a value of the number of character mismatches from the first state to the second state; and transitioning from the first state to a third state of the finite state machine, that is different from the second state, responsive to a mismatch between the one of the target sequence of characters and the respective one of the reference sequence of characters when in the first state and increasing the value of the number of character mismatches from the first state to the third state, wherein the target sequence of characters is determined to be included in a string within the genome if the value of the number of character mismatches is within a specified Hamming distance from the string within the genome.

2. The method of claim 1, further comprising:

comparing, in the second state, a next one of the target sequence of characters to a respective next one of the reference sequence of characters;

transitioning from the first state to a second state of the finite state machine responsive to a match between the next one of the target sequence of characters and the respective next one of the reference sequence of characters when in the second state; and transitioning from the second state to a fourth state of the finite state machine, that is different from the third state, responsive to a mismatch between the next one of the target sequence of characters and the respective next one of the reference sequence of characters when in the second state.

3. The method of claim 1, wherein the one of the target sequence of characters is a final one of the target sequence of characters, and wherein the target sequence of characters is determined to not comprise an off-target sequence to the string within the reference sequence of characters if the value of the number of character mismatches is greater than the specified Hamming distance from the string within the reference sequence of characters, and reporting that the genome does not comprise an off-target site if the number of character mismatches is less than the specified Hamming distance from no more than one string of reference sequence characters comprising the genome.

4. The method of claim 2, wherein transitioning from the second state to the third state further comprises:

maintaining a value of the number of character mismatches from the first state to the second state.

5. The method of claim 4, wherein transitioning from the second state to the fourth state further comprises:

increasing the value of the number of character mismatches from the first state to the third state.

6. The method of claim 1, wherein the memory and at least one processor on which the finite state machine operates comprises a plurality of sequential logic circuits each clocked by a clock signal, the plurality of sequential logic circuits having a plurality of input signals indicating a present state of the finite state machine and including a value of the one of the target sequence of characters and including a value of the respective one of the reference sequence of characters.

7. The method of claim 1, wherein the nucleic acid sequences are DNA sequences.

8. The method of claim 1, wherein the determining includes comparing the nucleic acid sequence of the target sequence of characters to the nucleic acid sequence of the reference sequence of characters and its complementary sequence.

9. A system comprising a memory and at least one processor coupled to the memory, the memory and at least one processor comprising:

a plurality of sequential logic circuits on which a finite state machine operates, wherein the finite state machine is configured to determine if a target sequence of characters is included in a string within a reference sequence of characters using states indicated by the plurality of sequential logic circuits to indicate a number of character mismatches between the target sequence of characters and the string within the reference sequence of characters, wherein the target sequence of characters and the string within the reference sequence of characters are nucleic acid sequences, and wherein the reference sequence of characters comprise a genome, wherein the plurality of sequential logic circuits are each clocked by a clock signal, the plurality of sequential logic circuits having a plurality of input signals indicating a present state of the finite state machine and including a value of one of a target sequence of characters and including a value of a respective one of a reference sequence of characters, and wherein the plurality of sequential logic circuits are configured to:

compare, in a first state of the finite state machine, one of the target sequence of characters to a respective one of the reference sequence of characters;

transition from the first state to a second state of the finite state machine responsive to a match between the one of the target sequence of characters and the respective one of the reference sequence of characters when in the first state and maintain a value of the number of character mismatches from the first state to the second state;

transition from the first state to a third state of the finite state machine, that is different from the second state, responsive to a mismatch between the one of the target sequence of characters and the respective one of the reference sequence of characters when in the first state and increase the value of the number of character mismatches from the first state to the third state; and determine that the target sequence of characters is included in a string within the genome if the value of the number of character mismatches is within a specified Hamming distance from the string within the genome.

10. The system of claim 9, wherein the plurality of sequential logic circuits are further configured to:

compare, in the second state, a next one of the target sequence of characters to a respective next one of the reference sequence of characters;

transition from the first state to a second state of the finite state machine responsive to a match between the next one of the target sequence of characters and the respective next one of the reference sequence of characters when in the second state; and transition from the second state to a fourth state of the finite state machine, that is different from the third state, responsive to a mismatch between the next one of the target sequence of characters and the respective next one of the reference sequence of characters when in the second state.

11. The system of claim 9, wherein the transition from the first state to the second state and the transition from the first state to the third state occur in a single cycle of a clock signal used to clock the finite state machine.

12. The system of claim 9, wherein the system is configured to determine if a target sequence of characters is included in a string within a reference sequence of characters by:
  performing a cross-correlation by comparing the target sequence of characters to the string within the reference sequence of characters in parallel with one another to indicate a number of character mismatches between the target sequence of characters and the string within the reference sequence of characters,
  wherein comparing the target sequence of characters to the string within the reference sequence of characters in parallel with one another comprises comparing codes corresponding to the target sequence of characters to codes corresponding to the string within the reference sequence of characters,
  and wherein determining that the target sequence of characters is included in the string within the reference sequence of characters occurs if the codes corresponding to the target sequence of characters are within a specified Hamming distance from the codes corresponding to the string within the genome.

13. The system of claim 9, wherein the nucleic acid sequences are DNA sequences.

14. A method of operating a finite state machine on a system comprising a memory and at least one processor coupled to the memory and configured to perform a method to determine if a target nucleic acid sequence is included in a string of nucleobases within a genome using states indicated by the finite state machine to indicate a number of mismatches between the target nucleic acid sequence and the string of nucleobases within the genome, the method comprising:
  comparing, in a first state of the finite state machine, a nucleobase of the target nucleic acid sequence to a respective nucleobase of the genome;
  transitioning from the first state to a second state of the finite state machine responsive to a match between the nucleobase of the target nucleic acid sequence and the respective nucleobase of the genome when in the first state and maintaining a value of the number of mismatches from the first state to the second state;
  transitioning from the first state to a third state of the finite state machine, that is different from the second state, responsive to a mismatch between the nucleobase of the target nucleic acid sequence and the respective nucleobase of the genome when in the first state and increasing the value of the number of mismatches from the first state to the third state; and
  determining that the target nucleic acid sequence is included in a string of nucleobases within the genome if the value of the number of mismatches is within a specified Hamming distance from the string of nucleobases within the genome.

15. The method of claim 14, further comprising:
  comparing, in the second state, a next nucleobase of the target nucleic acid sequence to a respective next nucleobase of the string within the genome;
  transitioning from the first state to a second state of the finite state machine responsive to a match between the next nucleobase of the target nucleic acid sequence and the respective next nucleobase of the string within the genome when in the second state; and
  transitioning from the second state to a fourth state of the finite state machine, that is different from the third state, responsive to a mismatch between the next nucleobase of the target nucleic acid sequence and the respective next nucleobase of the string within the genome when in the second state.

16. The method of claim 14, wherein the method further comprises:
  determining that the target nucleic acid sequence is not included in a string of nucleobases within the genome if the value of the number of mismatches exceeds the specified Hamming distance.

17. The method of claim 14, wherein the method further comprises, determining that the genome comprises at least one off-target site if the target nucleic acid sequence is within the specified Hamming distance of more than one string of nucleobases within the genome.

18. The method of claim 14, wherein the target nucleic acid sequence comprises a gRNA sequence.

* * * * *